(12) United States Patent
Langley et al.

(10) Patent No.: US 7,695,456 B2
(45) Date of Patent: Apr. 13, 2010

(54) MEDICAMENT DELIVERY DEVICE

(75) Inventors: Christopher Nigel Langley, Warwickshire (GB); Robert Frederick Veasey, Warwickshire (GB)

(73) Assignee: DCA Design International Limited, Warwick (GB)

( * ) Notice: Subject to any disclaimer, the term of this patent is extended or adjusted under 35 U.S.C. 154(b) by 1795 days.

(21) Appl. No.: 10/347,634

(22) Filed: Jan. 22, 2003

(65) Prior Publication Data
US 2003/0158524 A1 Aug. 21, 2003

(30) Foreign Application Priority Data
Jan. 25, 2002 (GB) ................................ 0201686.3

(51) Int. Cl.
*A61M 5/00* (2006.01)
(52) U.S. Cl. ...................... 604/218; 604/154; 604/155; 604/131
(58) Field of Classification Search ................ 604/218, 604/68, 69, 70, 97.02, 187, 223, 243, 207, 604/211, 131, 152, 35, 37, 151; 411/14; 73/761
See application file for complete search history.

(56) References Cited

U.S. PATENT DOCUMENTS

| 4,973,318 | A | | 11/1990 | Holm et al. | |
|---|---|---|---|---|---|
| 5,104,380 | A | * | 4/1992 | Holman et al. | 604/117 |
| 5,114,406 | A | | 5/1992 | Gabriel et al. | |
| 5,304,152 | A | * | 4/1994 | Sams | 604/207 |
| 5,674,205 | A | * | 10/1997 | Pasricha et al. | 604/232 |
| 5,808,203 | A | * | 9/1998 | Nolan et al. | 73/700 |
| 5,820,602 | A | * | 10/1998 | Kovelman et al. | 604/187 |
| 5,879,360 | A | | 3/1999 | Crankshaw | |
| 6,001,089 | A | * | 12/1999 | Burroughs et al. | 604/506 |
| 6,280,421 | B1 | * | 8/2001 | Kirchhofer et al. | 604/218 |
| 6,811,548 | B2 | * | 11/2004 | Jeffrey | 604/207 |
| 6,958,053 | B1 | * | 10/2005 | Reilly | 604/154 |
| 2001/0034502 | A1 | | 10/2001 | Moberg et al. | |

FOREIGN PATENT DOCUMENTS

| EP | 0 554 996 A1 | 8/1993 |
|---|---|---|
| GB | 2 300 926 A | 11/1996 |
| HU | 184 654 B | 1/1988 |
| HU | 206272 B | 10/1992 |
| HU | 219 515 B | 4/2001 |
| WO | WO 97/36623 | 10/1997 |
| WO | WO 01/37905 | 5/2001 |
| WO | WO 03/061737 A3 | 7/2003 |

* cited by examiner

*Primary Examiner*—Nicholas Lucchesi
*Assistant Examiner*—Laura A Bouchelle
(74) *Attorney, Agent, or Firm*—Oliff & Berridge, PLC

(57) ABSTRACT

The present invention relates to a medicament delivery device such as a pen type injector used to expel medicament from a medicament cartridge under the action of a lead screw. The medicament cartridge typically comprises a cylinder having a displaceable piston at one end displacement causing medicament contained within the cartridge to be expelled. It is of advantage to know when the plunger contacts the displaceable piston since no delivery of medicament can occur before this point. A delivery device is disclosed in which a lead screw for a medicament delivery device comprises a shaft portion and a head portion, the head portion further comprising a fixed part, a displaceable part movable with respect to the fixed part, biasing means acting normally to urge the displaceable part away from the fixed part and a sensor to detect when the displaceable part moves towards the fixed part, one of the fixed part and the displaceable part being provided with a plurality of resilient fingers extending axially with respect to the lead screw, and the other of the fixed part and the displaceable part being provided with a plurality of opening, each of the resilient fingers extending within a corresponding opening.

16 Claims, 2 Drawing Sheets

MEDICAMENT DELIVERY DEVICE

The present invention relates to a medicament delivery device and has particular, but not exclusive, application to injectors of the kind used for the self-administration of a medicament such as injectors of the kind known as pen type injectors. Such devices are often used by those with diabetes for the self-administration of one or more kinds of insulin.

It is known to provide a medicament delivery device in which medicament is expelled from a medicament cartridge under the action of a lead screw or plunger. The medicament cartridge typically comprises a cylinder having a displaceable piston at one end displacement of which in use causes medicament contained within the cartridge to be expelled. In particular, it is of advantage to know when contact has been made by the plunger with the displaceable piston since no delivery of medicament can occur before this point.

According to a first aspect of the invention, a lead screw for a medicament delivery device comprises a shaft portion and a head portion, the head portion further comprising a fixed part, a displaceable part movable with respect to the fixed part, biasing means acting normally to urge the displaceable part away from the fixed part and a sensor to detect when the displaceable part moves towards the fixed part, in which one of the fixed part and the displaceable part is provided with a plurality of resilient fingers extending axially with respect to the lead screw, and the other of the fixed part and the displaceable part is provided with a plurality of openings, each of the resilient fingers extending within a corresponding opening.

Preferably, the biasing means is incorporated within the sensor.

More preferably, between each of the plurality of resilient fingers there are located a plurality of axially extending channels, and the other of the fixed part and the displaceable part is provided with a plurality of projecting parts for sliding engagement within the channels.

Conveniently, each of the resilient fingers is provided with a radially outward extending tab.

Conveniently, the shaft portion of the lead screw is provided with a groove along its length. More preferably, a lead extends from the sensor along the shaft portion of the lead screw within the groove.

According to a second aspect of the invention, a medicament delivery device comprises a drive means by which a lead screw in accordance with the first aspect of the invention can be advanced in use to cause a medicament to be expelled from the medicament delivery device.

The invention will now be described, by way of example only, with reference to the accompanying drawings, in which.

Figures 1, 2:
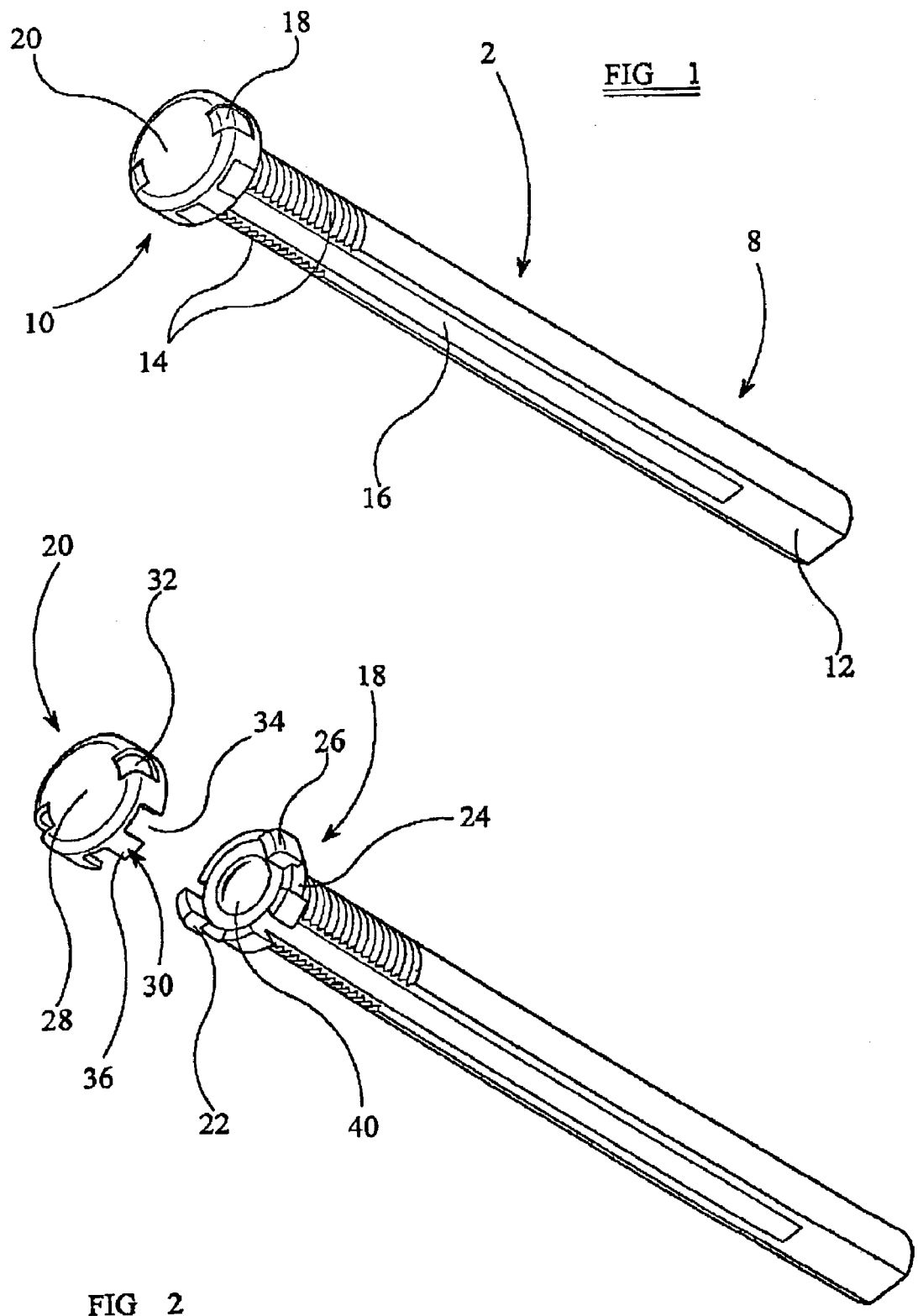
FIG. 1 shows a perspective view of a lead screw in accordance with the present invention.
FIG. 2 shows a similar view to that of FIG. 1 with a displaceable part removed from a fixed part of a head portion of the lead screw.
Figure 3:
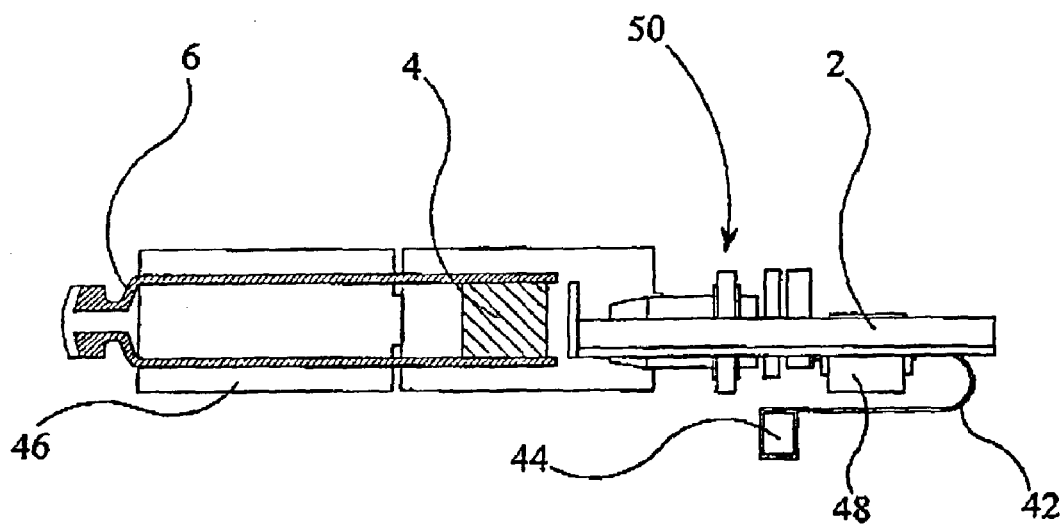
FIG. 3 shows a side view of the lead screw of the present invention implemented in a medicament delivery device showing the lead screw in a retracted position.
Figure 4:
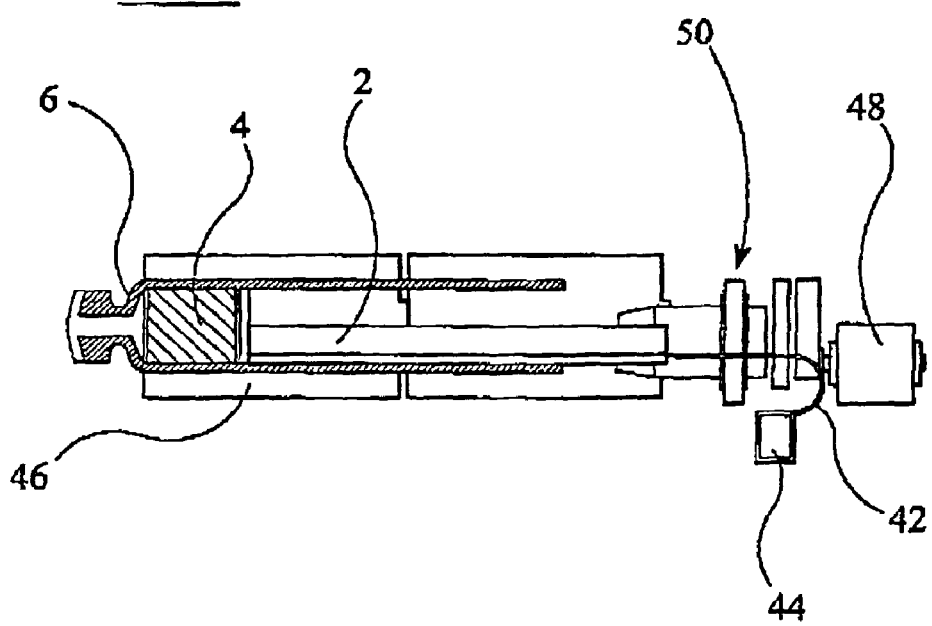
FIG. 4 shows a view similar to that of FIG. 3 with the lead screw in a fully advanced position.

Referring first to FIGS. 1 and 2, there may be seen a lead screw 2 for use with a medicament delivery device. In use, the lead screw 2 is adapted to be driven into contact with a piston 4 located within a medicament cartridge 6 in order to advance the piston within the medicament cartridge in order to displace a medicament from within the medicament cartridge (such a cartridge is shown in FIGS. 3 and 4).

The lead screw 2 comprises a shaft portion 8 and a head portion 10 at a first end of the shaft portion 8. The shaft portion has 8 two opposing flat sides 12 extending along a length thereof. Located between the opposing flat sides there are arcuate surfaces provided with a screw thread 14 extending therealong. For reasons of clarity a small part only of the screw thread 14 is shown in FIGS. 1 and 2. It will be understood that in practice the screw thread 14 extends substantially along the length of the lead screw 2.

One of the two opposing flat sides 12 of the lead screw 2 is provided with a channel or groove 16. The groove 16 extends substantially along the lead screw 2. In the embodiment illustrated in FIGS. 1 and 2, the groove 16 extends from the head portion 10 of the lead screw 2 almost to a second end of the shaft portion 8. In an alternative embodiment (not shown) the groove 16 may run along the whole length of the shaft portion 8.

The head portion 10 of the lead screw 2 comprises two parts; a fixed part 18 connected to the shaft portion 8 of the lead screw 2 and a displaceable part 20 retained upon the fixed part 18.

The fixed part 18 is generally circular in cross section and is connected to the shaft portion 8 at a circumferential region of the fixed part 18. An edge of the fixed part 18 is further provided with a plurality of resilient fingers 22 extending away from the shaft portion 8 of the lead screw 2. Between the plurality of resilient fingers 22 there are located a plurality of axially extending channels 24 in the fixed part. Each of the resilient fingers 22 is provided with a radially outward extending tab 26.

The displaceable part 20 comprises a flat portion 28 of section corresponding to that of the fixed part. The flat part 28 is provided with a skirt 30 extending about an edge of thereof. Between the skirt 30 and the flat part 28 are provided a plurality of openings 32. The skirt 30 is further provided with a number of cut away regions 34 about a periphery thereof thereby to form a number of projecting parts 36 of the skirt 30.

In use, the displaceable part 20 is retained upon the fixed part 18 by placing the displaceable part 20 onto the fixed part 18 such that each of the resilient fingers 22 extends through a corresponding opening 32 and each of the projecting parts 36 of the skirt 30 may be received within a corresponding axially extending channel 24. The tabs 26 on the fingers 22 act to provide a stop against which the skirt 30 will abut to limit the travel of the displaceable part 20 with respect to the fixed part 18 and to prevent the displaceable part 20 becoming free of the fixed part 18 once assembled thereon.

The length of each of the resilient fingers 22, the shape and size of the openings 32, together with the location of the tabs 26 on the resilient fingers 22 will be understood to be chosen so as to permit some relative motion between the fixed part 18 of the lead screw head portion 10 and the displaceable part 20.

A sensor 40 will, in use, be provided between the fixed part 18 of the lead screw head portion 10 and the displaceable part 20 in order to detect relative movement between the respective parts. In the context of the present invention, such relative movement should occur when the head portion 10 of the lead screw 2 is advanced into contact with the medicament cartridge piston 4. In order to prevent inadvertent actuation of the sensor biasing means should be located between the fixed part 18 and the displaceable part 20 of the lead screw head portion 10. Such biasing means may form part of the sensor 40. For example, the sensor 40 may take the form of a dome switch.

The sensor 40 will be provided with a lead 42 for connection to a central control unit or processor 44. When used with the illustrated lead screw (see for example FIG. 2), the lead 42 may conveniently be located within the lead screw groove 16. An example of a medicament delivery device showing this is shown in FIGS. 3 and 4.

In FIGS. 3 and 4 there are shown a number of elements making up a medicament delivery device. The medicament delivery device is provided with a power source such as batteries 46. The batteries 46 may be used to power a motor 48, the central control unit or processor (shown somewhat schematically as box 44) and a display (not shown) by which information relating to the use and/or operation of the medicament delivery device may be communicated to a user. The medicament delivery device further comprises a drive train 50 driven from the motor 48 and a lead screw 2 as described above adapted to be driven axially by way of the drive train 50.

A medicament cartridge is shown in FIG. 3, the piston 4 of which is located at a fist end of the medicament cartridge 6. The lead screw 2 is in a retracted position spaced from the piston 4. The lead 42 may be seen to extend from within the lead screw 2 to the central control unit or processor 44.

In FIG. 4, the lead screw 2 has been advanced to drive the piston 4 within the medicament cartridge 6 towards a second end of the medicament cartridge 6. In this position substantially all of the medicament will have been expelled from the medicament cartridge 6 through a needle unit (not shown) located at the second end of the medicament cartridge 6. Again the lead 42 from the sensor 40 may be seen to extend from within the lead screw 2 to the central control unit or processor 44.

It will be understood that the use of this sensor 40 having such a flexible lead 42 in conjunction with the groove 16 in the lead screw 2 allows for a compact arrangement of the components within the medicament delivery device.

Where a medicament cartridge of standard dimensions is used, the location of the second end of the medicament cartridge 6 is known within the medicament delivery device. During manufacture the location of the lead screw 2 within the medicament delivery device will be calibrated. Since the thread of the lead screw 2 is fixed, actuation of the motor 48 for a predetermined period will correspond to a fixed movement of the lead screw 2. Thus, when the sensor 40 indicates that the head portion 10 of the lead screw 2 has contacted the medicament cartridge piston 4, the position of the lead screw 2 and hence the piston 4 within the medicament cartridge 6 can be determined by the central control unit or processor 44. This information can then be used to calculate the amount of medicament contained within the medicament cartridge 6.

The invention claimed is:

1. A lead screw for a medicament delivery device, comprising:
    a shaft portion; and
    a head portion, the head portion further comprising:
        a fixed part,
        a displaceable part movable with respect to the fixed part,
        biasing means acting normally to urge the displaceable part away from the fixed part, and
        a position sensor to detect when the displaceable part moves towards the fixed part, in which one of the fixed is provided with a plurality of resilient fingers extending axially with respect to a longitudinal axis of the lead screw, and displaceable part is provided with a plurality of openings, each of the resilient fingers extending within a corresponding opening.

2. A lead screw according to claim 1, in which the biasing means is incorporated within the sensor.

3. A lead screw according to claim 2, in which between each of the plurality of resilient fingers there are located a plurality of axially extending channels, and the displaceable part is provided with a plurality of projecting parts for sliding engagement within the channels.

4. A lead screw according to claim 1, in which between each of the plurality of resilient fingers there are located a plurality of axially extending channels, and the displaceable part is provided with a plurality of projecting parts for sliding engagement within the channels.

5. A lead screw according to claim 1, in which each of the resilient fingers is provided with a radially outward extending tab.

6. A lead screw according to claim 1, in which the shaft portion of the lead screw is provided with a groove along its length.

7. A lead screw according to claim 6, in which the sensor further comprises a lead extending from the sensor along the shaft portion of the lead screw within the groove.

8. A medicament delivery device comprising a drive means by which a lead screw in accordance with claim 1 can be advanced in use to cause a medicament to be expelled from the medicament delivery device.

9. A lead screw for a medicament delivery device, comprising:
    a shaft portion; and
    a head portion, the head portion further comprising:
        a fixed part,
        a displaceable part movable with respect to the fixed part,
        biasing means acting normally to urge the displaceable part away from the fixed part, and
        a position sensor to detect when the displaceable part moves towards the fixed part, in which one of the fixed part and the displaceable part is provided with a plurality of resilient fingers extending axially with respect to a longitudinal axis of the lead screw, and the other of the fixed part and the displaceable part is provided with a plurality of openings, each of the resilient fingers extending within a corresponding opening.

10. A lead screw according to claim 9, in which the biasing means is incorporated within the sensor.

11. A lead screw according to claim 10, in which between each of the plurality of resilient fingers there are located a plurality of axially extending channels, and the other of the fixed part and the displaceable part is provided with a plurality of projecting parts for sliding engagement within the channels.

12. A lead screw according to claim 9, in which between each of the plurality of resilient fingers there are located a plurality of axially extending channels, and the other of the fixed part and the displaceable part is provided with a plurality of projecting parts for sliding engagement within the channels.

13. A lead screw according to claim 9, in which each of the resilient fingers is provided with a radially outward extending tab.

14. A lead screw according to claim 9, in which the shaft portion of the lead screw is provided with a groove along its length.

15. A lead screw according to claim 14, in which the sensor further comprises a lead extending from the sensor along the shaft portion of the lead screw within the groove.

16. A medicament delivery device comprising a drive means by which a lead screw in accordance with claim 9 can be advanced in use to cause a medicament to be expelled from the medicament delivery device.

\* \* \* \* \*